US012731687B2

(12) United States Patent
Glass et al.

(10) Patent No.: US 12,731,687 B2
(45) Date of Patent: Sep. 8, 2026

(54) SYSTEMS AND METHODS FOR MACHINE LEARNING (ML) MODEL DIAGNOSTIC ASSESSMENTS BASED ON DIGITAL PATHOLOGY DATA

(71) Applicant: PathAI, Inc., Boston, MA (US)

(72) Inventors: Benjamin Glass, Boston, MA (US); Surya Teja Chavali, Boston, MA (US); Syed Ashar Javed, Boston, MA (US); Shamira Sridharan Weaver, Boston, MA (US); Murray Resnick, Boston, MA (US); Ilan Wapinski, Brookline, MA (US); Michael Montalto, Boston, MA (US); Andrew Hanno Beck, Brookline, MA (US); Aditya Khosla, Watertown, MA (US)

(73) Assignee: PATHAI, INC., Boston, MA (US)

( * ) Notice: Subject to any disclaimer, the term of this patent is extended or adjusted under 35 U.S.C. 154(b) by 877 days.

(21) Appl. No.: 17/747,536

(22) Filed: May 18, 2022

(65) Prior Publication Data

US 2022/0375606 A1 Nov. 24, 2022

Related U.S. Application Data

(60) Provisional application No. 63/190,162, filed on May 18, 2021.

(51) Int. Cl.

| | |
|---|---|
| ***G16H 50/20*** | (2018.01) |
| ***G06T 7/00*** | (2017.01) |

(Continued)

(52) U.S. Cl.

CPC ........... *G16H 50/20* (2018.01); *G06T 7/0012* (2013.01); *G06V 10/25* (2022.01); *G16H 70/60* (2018.01); *G06T 2207/30096* (2013.01)

(58) Field of Classification Search

CPC ........ G16H 50/20; G16H 70/60; G16H 10/20; G16H 20/10; G16H 30/40; G16H 50/30;

(Continued)

(56) References Cited

U.S. PATENT DOCUMENTS

| | | | |
|---|---|---|---|
| 10,650,520 | B1 | 5/2020 | Beck et al. |
| 10,957,041 | B2 | 3/2021 | Yip et al. |

(Continued)

FOREIGN PATENT DOCUMENTS

| | | | |
|---|---|---|---|
| EP | 3576096 | A1 | 12/2019 |
| WO | WO-2020150258 | A1 | 7/2020 |

(Continued)

OTHER PUBLICATIONS

Robinson, Max, et al. "Quality assurance guidance for scoring and reporting for pathologists and laboratories undertaking clinical trial work." The Journal of Pathology: Clinical Research 5.2 (2019): 91-99.https://pathsocjournals.onlinelibrary.wiley.com/doi/full/10.1002/cjp2.121 (Year: 2019).*

(Continued)

*Primary Examiner* — Han Hoang

(74) *Attorney, Agent, or Firm* — Wilmer Cutler Pickering Hale and Dorr LLP

(57) ABSTRACT

Techniques for performing diagnostic assessments based on digital pathology data are disclosed. In one particular embodiment, the techniques may be realized as a method for performing a diagnostic assessment based on digital pathology data comprising obtaining first digital pathology data comprising intensity information, the first digital pathology data being associated with a plurality of regions of interest in a biological sample; applying first machine learning models to the first digital pathology data, the first machine learning models identifying first regions of interest among the plurality of regions of interest based on the intensity (Continued)

information; applying second machine learning models to the first digital pathology data, the second machine learning models identifying at least one pattern associated with at least one of the first regions of interest; generating a diagnostic assessment based on the first regions of interest and the at least one pattern.

28 Claims, 6 Drawing Sheets

(51) Int. Cl.
*G06V 10/25* (2022.01)
*G16H 70/60* (2018.01)

(58) Field of Classification Search
CPC ...... G16H 50/70; G16H 30/20; G06T 7/0012; G06T 2207/30096; G06T 2207/10056; G06T 2207/20084; G06T 2207/30024; G06V 10/25; G06V 20/695; G06V 20/698; G06N 3/0464; G06N 3/09
See application file for complete search history.

(56) References Cited

U.S. PATENT DOCUMENTS

| | | | |
|---|---|---|---|
| 10,991,097 B2 | 4/2021 | Yip et al. | |
| 11,640,859 B2 | 5/2023 | Colley et al. | |
| 12,112,839 B2 | 10/2024 | Colley et al. | |
| 12,175,666 B2 | 12/2024 | Wang et al. | |
| 2012/0076390 A1* | 3/2012 | Potts | G06T 7/38 382/133 |
| 2015/0110381 A1 | 4/2015 | Parvin et al. | |
| 2016/0027226 A1 | 1/2016 | Gigl et al. | |
| 2016/0110584 A1 | 4/2016 | Remiszewski et al. | |
| 2016/0267226 A1* | 9/2016 | Xu | G16H 15/00 |
| 2017/0212018 A1* | 7/2017 | Grunkin | G06T 7/0014 |
| 2018/0232883 A1 | 8/2018 | Sethi et al. | |
| 2020/0150258 A1 | 5/2020 | Itkin | |
| 2020/0258223 A1 | 8/2020 | Yip | |
| 2020/0294231 A1 | 9/2020 | Tosun et al. | |
| 2020/0342597 A1 | 10/2020 | Chukka et al. | |
| 2021/0073986 A1* | 3/2021 | Kapur | G16H 50/20 |
| 2021/0093249 A1* | 4/2021 | Anand | G16H 50/20 |
| 2022/0245802 A1 | 8/2022 | Wang et al. | |
| 2022/0375606 A1 | 11/2022 | Glass | |

FOREIGN PATENT DOCUMENTS

| | | |
|---|---|---|
| WO | WO-2022038527 A1 | 2/2022 |
| WO | WO-2022165433 A1 | 8/2022 |
| WO | WO-2022245925 A1 | 11/2022 |

OTHER PUBLICATIONS

International Search Report and Written Opinion issued by the U.S. Patent and Trademark Office as International Searching Authority in Interntaional Application No. PCT/US22/29807, dated Sep. 23, 2022 (10 pages).

Glass, et al., "Abstract #3061: Machine Learning Models to Quantify HER2 for Real-Time Tissue Image Analysis in Prospective Clinical Trials", American Society of Clinical Oncology Annual Meeting, Virtual Meeting, Jun. 4-8, 2021 (1 page).

Marchio, et al., "Evolving concepts in HER2 evaluation in breast cancer: Heterogeneity, HER2-low carcinomas and beyond", Seminars in Cancer Biology, 72:123-135, available online Feb. 26, 2020 (13 pages).

Modi, et al., "Trastuzumab Deruxtecan in Previously Treated HER2-Positive Breast Cancer", New England Journal of Medicine, 382(7):610-621, 2020, available Dec. 11, 2019 (12 pages).

Perez, et al., "HER2 Testing by Local, Central, and Reference Laboratories in Specimens From the North Central Cancer Treatment Group N9831 Intergroup Adjuvant Trial", Journal of Clinical Oncology, 24(19):3032-3038, Jul. 1, 2006 (7 pages).

Adnan, et al., "Representation Learning of Histopathology Images using Graph Neural Networks", IEEE/CVF Conference on Computer Vision and Pattern Recognition Workshops (CVPRW), pp. 4254-4261, 2020 (8 pages).

Diehl, "Edge Contraction Pooling for Graph Neural Networks", https://arxiv.org/pdf/1905.10990, May 27, 2019 (9 pages).

European Extended Search Report issued in European Application No. EP22746881.6, dated Oct. 24, 2024 (9 pages).

International Search Report and Written Opinion issued by the U.S. Patent and Trademark Office in International Application No. PCT/US22/14778, dated May 12, 2022 (11 pages).

Krizhevsky, et al., "ImageNet Classification with Deep Convolutional Neural Networks", original version published in Proceedings of the 25th International Conference on Neural Information Processing Systems, Lake Tahoe, NV, pp. 1097-1105, Dec. 2012,, Communications of the ACM, 60(6):84-90, Jun. 2017 (7 pages).

Lee, et al., "Self-Attention Graph Pooling", Proceedings of the 36th International Conference on Machine Learning, Long Beach, California, PMLR97, https://arXiv:1904.08082v4, Jun. 13, 2019 (10 pages).

Levy, et al., "A large-scale internal validation study of unsupervised virtual trichrome staining technologies on nonalcoholic steatohepatitis liver biopsies", Modern Pathology, 34:808-822, 2021, published online Dec. 9, 2020 (15 pages).

Morris, et al., "Weisfeiler and Leman Go Neural: Higher-Order Graph Neural Networks," Association for the Advancement of Artificial Intelligence, Thirty-Third AAAI Conference on Artificial Intelligence (AAAI-19), 33(01), 4602-4609, 2019 (8 pages).

Szegedy, et al., "Going Deeper with convolutions," 2015 IEEE Conf. on Computer Vision and Pattern Recognition, https://arXiv:1409.4842v1, Sep. 17, 2014 (12 pages).

Wang, et al., "Face Search at Scale: 80 Million Gallery", MSU Technical Report MSU-CSE-15- 11, https://arXiv:1507.07242v2, Jul. 24, 2015 (15 pages).

Zhang, et al., "BIRCH: An Efficient Data Clustering Method for Very Large Databases," Proc. 1996 ACM SIGMOD Intl. Conf. on Management of Data, Montreal, Canada, 103-114, 1996 (12 pages).

Khameneh, et al., "Automated segmentation of cell membranes to evaluate HER2 status in whole slide images using a modified deep learning network", Computers in Biology and Medicine, 110:164-174, 2019 (11 pages).

Masmoudi, et al., "Automated Quantitative Assessment of HER-2/neu Immunohistochemical Expression in Breast Cancer", IEEE Transactions on Medical Imaging, 28(6):916-925, Jun. 2009 (10 pages).

Qaiser, et al., "Learning Where to See: A Novel Attention Model for Automated Immunohistochemical Scoring", IEEE Transactions on Medical Imaging, 38(11):2620-2631, Nov. 2019 (12 pages).

Vandenberghe, et al., "Relevance of deep learning to facilitate the diagnosis of HER2 status in breast cancer", Scientific Reports, 7:45938, Apr. 5, 2017 (11 pages).

European Extended Search Report issued in European Patent Application EP22805386.4, dated Mar. 14, 2025 (17 pages).

Robinson, et al., "Quality assurance guidance for scoring and reporting for pathologists and laboratories undertaking clinical trial work", Journal of Pathology: Clinical Research, 5:91-99, Apr. 2019, published online Nov. 29, 2018 (9 pages).

* cited by examiner

PathAI
120 Brookline Avenue
Boston, MA 02215
617-500-8457

Anti-HER2/neu (4B5) in Breast Cancer
Generated 09/22/2020 9:20PM UTC

Patient ID Demo-09 Sample ID Demo0901 HER2 WSI ID Demo-09

Algorithm PAI-QC-HER2-BCa-v1.0 WSI Received 09/22/2020 9:20PM UTC Trial Platform v. 20200826

PathAI Algorithm PAI-QC-HER2-BCa-v1.0 Results

| | |
|---|---|
| PathAI Adjusted HER2 Score | 2+ |
| PathAI Precision HER2 Score | 2+ |
| Tumor area (%) | 11.3 |
| Tumor cells (count) | 79217 |

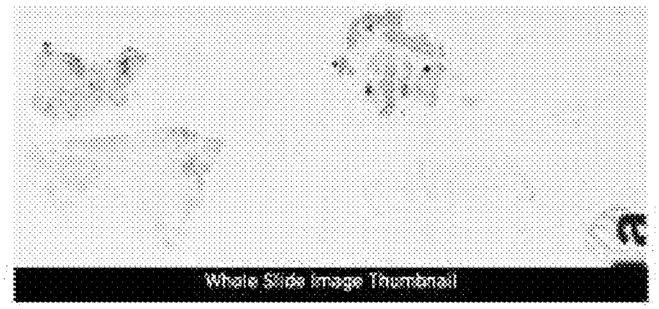

Whole Slide Image Thumbnail

DETAILED RESULTS

| | |
|---|---|
| Tumor cells with no membrane staining (%) | 9.3 |
| Tumor cells with faint/barely perceptive incomplete membrane staining (%) | 19.9 |
| Tumor cells with weak to moderate incomplete membrane staining (%) | 52.6 |
| Tumor cells with intense and incomplete membrane staining (%) | 17 |
| Tumor cells with faint/barely perceptive complete membrane staining (%) | 0.0 |
| Tumor cells with weak to moderate complete membrane staining (%) | 0.1 |
| Tumor cells with intense and complete circumferential staining (%) | 4.9 |
| Minimum HER2 staining intensity in tumor region | Negative |
| Maximum HER2 staining intensity in tumor region | Intense |
| Proportion of Normal area above weak staining intensity (%) | 2.8 |
| DCIS area (%) | 13 |
| Proportion of DCIS area above weak staining intensity (%) | 0.7 |
| PathAI Result turn-around time (TAT)* | 78 min |
| Artifact area (%) | 29.5 |
| Tumor area (mm^2) | 15.1 |

**Turn around time is measured as the time from when the HER2 whole slide image upload to PathAI QC tool is complete to generation of the final result from PAI-QC-HER2-BCa-v1.0.

PathAI interpretation of HER2 expression of Ventana anti-HER2/neu (4B5) assay was performed on whole slide images generated using the Aperio AT2 scanner at 40X magnification. Algorithm PAI-QC-HER2-BCa-v1.0 was run by pathaioperator@example.com.

See appendices for protocol

FIG. 4

Summary Definitions for the Ultra-Low/Low HER2 Scoring Criterion

| Score: 0 | Score: >0 <1+ | Score: 1+ | Score: 2+ | Score: 3+ |
|---|---|---|---|---|
| No staining | ♠ >1% ≤10% of tumor cells with faint partial membrane staining<br>AND/OR<br>♦ >1% ≤10% of tumor cells with moderate partial membrane staining<br>AND/OR<br>▲ >1% ≤10% of tumor cells with intense partial membrane staining<br>AND/OR<br>♣ >1% ≤10% of tumor cells with faint complete membrane staining<br>AND/OR<br>♥ >1% ≤10% of tumor cells with moderate complete membrane staining | ♠ >10% of tumor cells with faint partial membrane staining<br>AND/OR<br>♦ >10% of tumor cells with moderate partial membrane staining | ▲ >10% of tumor cells with intense partial membrane staining<br>AND/OR<br>♦ >10% of tumor cells with faint complete membrane staining<br>AND/OR<br>▲ >10% of tumor cells with moderate complete membrane staining<br>AND/OR<br>♣ >1% ≤10% of tumor cells with intense complete membrane staining | ♥ >10% of tumor cells with intense complete membrane staining |

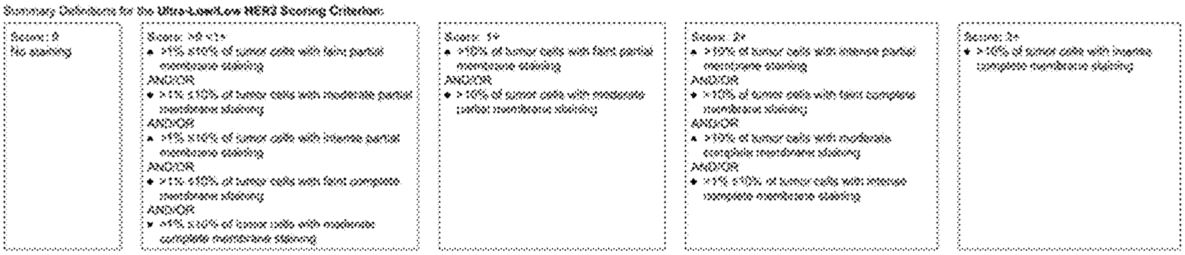

FIG. 6

SYSTEMS AND METHODS FOR MACHINE LEARNING (ML) MODEL DIAGNOSTIC ASSESSMENTS BASED ON DIGITAL PATHOLOGY DATA

CROSS-REFERENCE TO RELATED APPLICATIONS

The present application claims priority to U.S. Provisional Patent Application No. 63/190,162, entitled "Machine Learning (ML) Model Quality Control of HER2 Scoring in Diverse Breast Cancer Tissue Types," filed May 18, 2021, which is incorporated by reference herein in its entirety.

FIELD OF THE DISCLOSURE

The present disclosure generally relates to performing diagnostic assessments based on digital pathology data and more specifically to machine learning (ML) model diagnostic assessments, such as ML model quality control of human growth factor receptor 2 (HER2) scoring in diverse breast cancer tissue types.

BACKGROUND OF THE DISCLOSURE

The membrane receptor protein human epidermal growth factor receptor 2 (HER2) is overexpressed on cancer cells in 15%-20% of cases and is a demonstrated negative prognostic factor, causing activation of signaling pathways that regulate cell proliferation and survival. HER2 is therefore a target for anti-cancer compounds, and a growing number of HER2-targeting therapeutics have been developed, including monoclonal antibodies, kinase inhibitors, and antibody-drug conjugates, and are either currently on-market or under investigation in clinical trials. Today, in practice, every newly diagnosed breast carcinoma, as well as any relapses or metastatic deposits are assessed for HER2 status to assess patient eligibility for these HER2-targeting treatments. However, studies have shown that 4% of negative cases and 18% of positive cases are misdiagnosed. Furthermore, many patients with HER2-positive metastatic breast cancer progress after available treatments. These observations suggest that there is there is significant unmet need for improved diagnostics or alternative treatment options (or both) within this patient population.

SUMMARY OF THE DISCLOSURE

Techniques for ML model diagnostic assessments based on digital pathology data, such as whole slide images (WSIs), are disclosed. For illustrative purposes, the diagnostic assessments may include human epidermal growth factor receptor 2 (HER2) scoring. Those skilled in the art would appreciate that the techniques disclosed herein may be applied to other types of diagnostic assessments, as an alternative to or in addition to HER2 scoring.

In one particular embodiment, the techniques may be realized as a method for performing a diagnostic assessment based on digital pathology data, the method comprising obtaining first digital pathology data comprising intensity information, the first digital pathology data being associated with a plurality of regions of interest in a biological sample; applying one or more first machine learning models to the first digital pathology data, the one or more first machine learning models identifying one or more first regions of interest among the plurality of regions of interest based on the intensity information; applying one or more second machine learning models to the first digital pathology data, the one or more second machine learning models identifying at least one pattern associated with at least one of the one or more first regions of interest; generating a diagnostic assessment based on the one or more first regions of interest and the at least one pattern.

In accordance with other aspects of this particular embodiment, the first digital pathology data comprises one or more whole slide images. In some embodiments, the one or more whole slide images may correspond to a tumor biopsy sample stained using anti-HER2 immunohistochemistry.

In accordance with other aspects of this particular embodiment, the diagnostic assessment comprises a HER2 score.

In accordance with other aspects of this particular embodiment, the one or more first regions of interest comprises at least one of a tissue region of interest or a cell of interest. In some embodiments, the at least one of the tissue region of interest or the cell of interest may comprise one or more of a cancer epithelium, a cancer stroma, a ductal carcinoma in situ, a necrosis, a cell membrane, or an artifact.

In accordance with other aspects of this particular embodiment, the least one pattern comprises a staining pattern of a cell membrane. In some embodiments, the staining pattern may be selected from a group consisting of: negative or unstained, partial positive, and complete positive.

In accordance with other aspects of this particular embodiment, the diagnostic assessment comprises a precision slide-level score.

In accordance with other aspects of this particular embodiment, the diagnostic assessment comprises an adjusted slide level score, the adjusted slide level score being generated using machine learning model predictions optimized for consensus between the adjusted slide level score and a slide level score provided by a pathologist.

In accordance with other aspects of this particular embodiment, the method further comprises applying one or more third machine learning models to the first digital pathology data, the one or more third machine learning models identifying an intensity associated with at least one of the one or more first regions of interest. In some embodiments, the intensity may correspond to an intensity of staining of cell membranes, wherein the intensity is selected from a group consisting of: unstained, faintly stained, moderately stained, or completely stained.

In accordance with other aspects of this particular embodiment, the method further comprises extracting one or more histological features associated with the first digital pathology data.

In accordance with other aspects of this particular embodiment, the method further comprises calculating one or more cell-level features associated with the first digital pathology data. In some embodiments, the one or more cell-level features are based on a number of cells corresponding to each American Society of Clinical Oncology/College of American Pathologists (ASCO/CAP) category identified in the first digital pathology data.

In accordance with other aspects of this particular embodiment, the tumor biopsy sample is derived from a patient with breast cancer.

In accordance with other aspects of this particular embodiment, the method further comprises assessing drift in diagnostic assessments performed by pathologists in a clinical trial based on the generated diagnostic assessment.

In another particular embodiment, the techniques may be realized as a system for performing diagnostic assessments based on digital pathology data comprising at least one computer processor communicatively coupled to and configured to operate in the diagnostic assessment system, wherein the at least one computer processor is further configured to perform the steps in the above-described method.

In another particular embodiment, the techniques may be realized as an article of manufacture for performing diagnostic assessments based on digital pathology data with a diagnostic assessment system comprising a non-transitory processor readable medium and instructions stored on the medium, wherein the instructions are configured to be readable from the medium by at least one computer processor communicatively coupled to and configured to operate in the diagnostic assessment system and thereby cause the at least one computer processor to operate so as to perform the steps in the above-described method.

The present disclosure will now be described in more detail with reference to particular embodiments thereof as shown in the accompanying drawings. While the present disclosure is described below with reference to particular embodiments, it should be understood that the present disclosure is not limited thereto. Those of ordinary skill in the art having access to the teachings herein will recognize additional implementations, modifications, and embodiments, as well as other fields of use, which are within the scope of the present disclosure as described herein, and with respect to which the present disclosure may be of significant utility.

BRIEF DESCRIPTION OF THE DRAWINGS

To facilitate a fuller understanding of the present disclosure, reference is now made to the accompanying drawings, in which like elements are referenced with like numerals. These drawings should not be construed as limiting the present disclosure, but are intended to be illustrative only.

FIGS. 2-6 show illustrative experimental results according to some embodiments.

DETAILED DESCRIPTION

Figure 1:
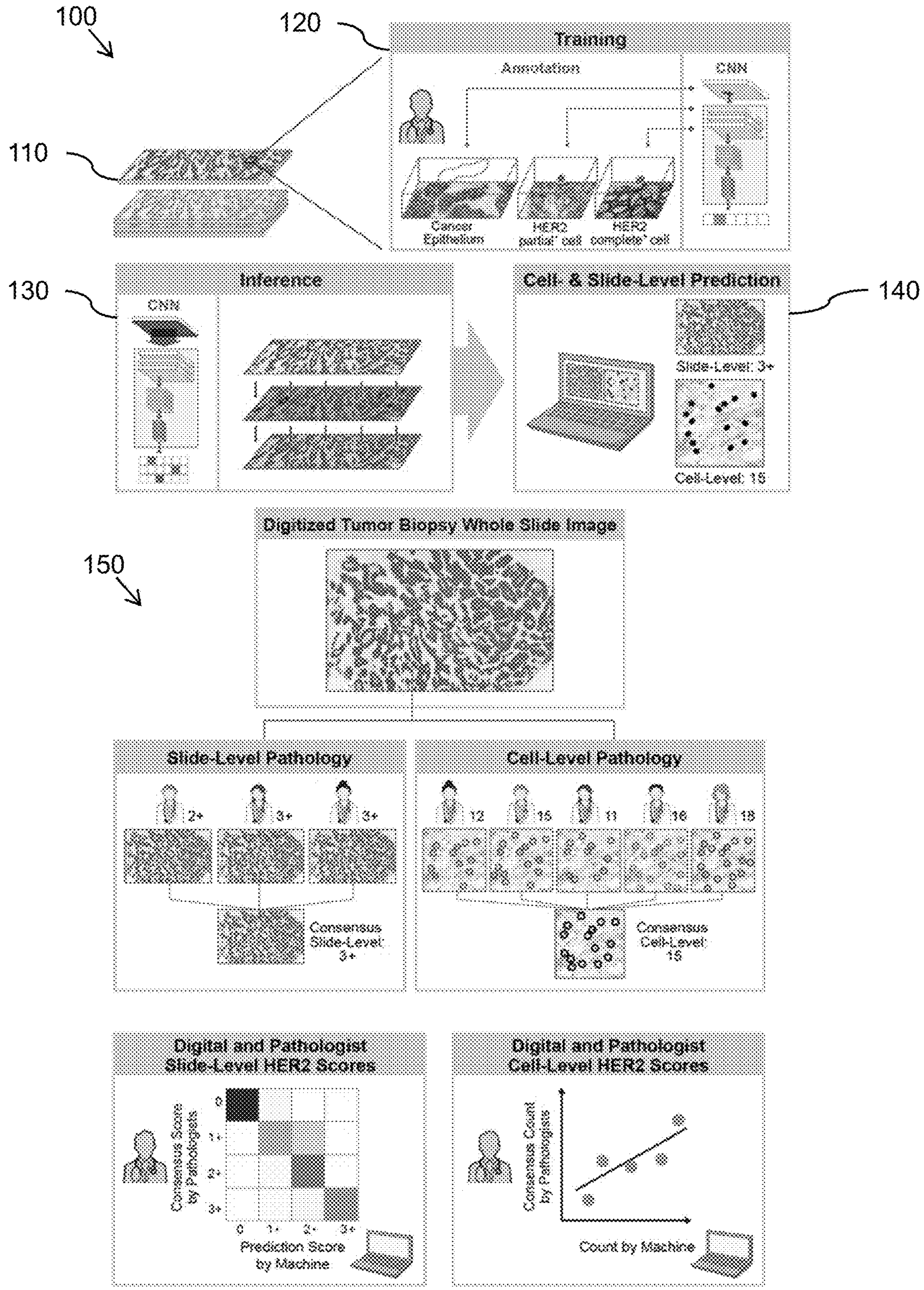
FIG. 1 shows a simplified diagram of a machine learning (ML) model training and validation method according to some embodiments.

In clinical practice, human epidermal growth factor receptor 2 (HER2) expression is defined in each case using the American Society of Clinical Oncology/College of American Pathologists (ASCO/CAP) scoring criteria where tumor tissues samples are stained to visualize HER2 and pathologists assign a score (0, 1+, 2+, or 3+) based on three factors: the membrane staining pattern (circumferential complete or incomplete), stain intensity (intense, moderate, or weak) and number of cells stained (with cut-offs of 0%, >10%, or <10% of tumor cells). ASCO/CAP guidelines for assigning a scores include vague descriptors of staining as "faint/barely perceptible", and "weak to moderate" which are subjective and difficult to differentiate. Additionally, using real-world samples that will have a wide range of tissue quality, it can be challenging for pathologists to distinguish between "complete" and "incomplete" membranous staining objectively and reproducibly. These challenges apply to HER2 scoring and other types of diagnostic assessments that are subject to analogous constrains, e.g., assessments in which the diagnostic classifications may be vague, subjective, or the like, and/or the diagnostic samples (e.g., tissue samples) may vary in quality and completeness.

The techniques disclosed herein provide, by way of illustration, a method for quantification of HER2 staining pattern and intensity in breast cancer tissue samples (HER2 stained with Ventana HER2 [4B5] Immunohistochemistry Assay) using ML algorithms to generate scores using the same parameters used to calculate ASCO/CAP HER2 scores. The algorithms also measure the tumor area, ductal carcinoma in situ (DCIS), and artifact content. According to some embodiments, the method may include one or more of the following processes:

Using expert pathologist annotations of histological features in digitized, anti-HER2 stained, whole slide images (WSIs) of a diverse breast cancer tissue dataset to train convolutional neural networks (CNNs) (or other suitable ML model types) to identify tissues and cell types of interest, as well as HER2 stain pattern and intensity; Deploying the pretrained CNNs on breast cancer tumor tissue WSI to generate HER2 scores equivalent to ASCO/CAP scores, as well as overlays of tissue histology features; and The ML model generating one or more HER2 scores for each slide—e.g., a precision score that is the direct readout from the ML model after training on pathologist annotations, and an adjusted score optimized to more closely match pathologist scoring, which is generated from the model after further training to learn pathologist scoring patterns and trends.

In one particular embodiment, the techniques may be realized as a method for automated quantification of HER2 to generate a HER2 ASCO/CAP score comprising: obtaining one or more whole slide images (WSIs) of a tumor biopsy sample from a clinical trial subject that has been stained using anti-HER2 immunohistochemistry; applying one or more first machine learning algorithms to the one or more WSIs to identify at least one of a tissue region or cell of interest, wherein the at least one of the tissue region or cell of interest comprises one or more of cancer epithelium, cancer stroma, ductal carcinoma in situ, necrosis, cell membrane, or artifacts; applying one or more second machine learning algorithms to the one or more WSIs to identify at least one pattern of HER2 staining of cell membranes, the at least one pattern comprising one or more of HER2 negative or unstained cells, HER2 partial positive, or HER2 complete positive cells; applying one or more third machine learning algorithms to the one or more WSIs to identify an intensity of HER2 staining of cell membranes, the intensity comprising one or more of unstained, faintly, moderately, or completely stained cell membranes; extracting one or more histological features for each of the one or more WSIs; calculating one or more cell-level features in each case that reflect the number of cells corresponding to each ASCO/CAP category present on the one or more WSIs; generating one or more precision slide-level scores for each of the one or more WSIs; and generating one or more adjusted slide-level scores for each of the one or more WSIs that are machine learning model predictions optimized for consensus between algorithm-generated slide-level score and pathologist provided slide-level score.

In accordance with other aspects of this particular embodiment, the tumor biopsy sample is derived from a patient with breast cancer.

In accordance with other aspects of this particular embodiment, the algorithms are trained using a diverse dataset of breast cancer tissue samples with a range of HER2 cores, and tumor grades, that were collected by various methods (biopsy, resection, core needle biopsy, or excision), from primary and metastatic tumors, with and without pre-invasive lesions.

In accordance with other aspects of this particular embodiment, the algorithms are trained to optimize predictions of ductal carcinoma in situ, and invasive ductal carcinoma.

In accordance with other aspects of this particular embodiment, an ultra-low HER2 score, not included in ASCO/CAP scoring guidelines, defined as >0<1+, is created.

In accordance with other aspects of this particular embodiment, drift in pathologist scoring of HER2 in clinical trials is assessed by integrating the above-described method into clinical trial workflow as a quality control tool.

FIG. 1 is a simplified diagram of a machine learning (ML) model training and validation method 100 according to some embodiments. Although FIG. 1 focuses on HER2 scoring an illustrative application of the disclosed method, those skilled in the art would understand that the method shown in FIG. 1 may be readily adapted to a wide variety of diagnostic assessments based on digital pathology data.

As shown in FIG. 1, ML models can be trained (block 120) to identify cells and tissue types within digitized whole slide images (WSI) 110 of tissues samples. The resulting ML models can count and quantify cells, tissues, and artifacts within WSI rapidly, accurately, and reproducibly, as well as assess stain quality (block 130). Application of ML models to quantification of HER2 and assignment of ML-ASCO/CAP scores (block 140) may standardize HER2 assessments as a resource to inform pathologist scoring of breast cancer tumor samples in prospective clinical trials. The reproducibility of the algorithm can enable trial sponsors to monitor inconsistencies (or "drift") in the manual scoring of the patient samples, enhancing the quality and potentially reducing the variability in these quantitative assessments.

In some embodiments, the method of FIG. 1 may involve the use of convolutional neural networks (CNNs) to digitally assess HER2 expression pattern and intensity in breast cancer tissue from digitized WSI of cancer tissue stained using immunohistochemistry to detect HER2 protein. In an illustrative embodiment tested experimentally, CNNs were trained using over 190,000 annotations of cells and tissue regions from 30 expert pathologists. As shown in FIG. 1, at block 120, a first CNN is trained to segment the slide into regions, such as cancer epithelium, cancer stroma, necrosis, and artifact regions. A second CNN is trained to differentiate tumor morphology, e.g., invasive versus noninvasive. For example, the second CNN may differentiate ductal carcinoma in situ at a lower magnification. A third CNN is trained to identify regions (e.g., cancer cells, other cells, cell membrane) and patterns associated with the regions (e.g., HER2 membrane staining pattern (complete, partial, or unstained)). A fourth CNN is trained to identify cell membranes. In some embodiments, a method for sampling from pathologists' annotations of cell membranes may be used to train the fourth CNN. These four models are illustrative, and according to some embodiments, different numbers and types of CNNs may be trained. Moreover, other types of neural networks may be used as an alternative to, or in addition to, CNNs.

For each individual cell, an intensity metric for each individual pixel corresponding to the cell membrane (e.g., a brownness metric) may be calculated. The metric is then aggregated across all membrane pixels corresponding to each cell to generate an intensity score (e.g., a brownness intensity score). These intensity scores may then be classified, e.g., bucketed into the categories such as intense, moderate, faint or weak. The classification thresholds (e.g., the thresholds used for bucketing) may be learned using human annotations.

Figure 2:
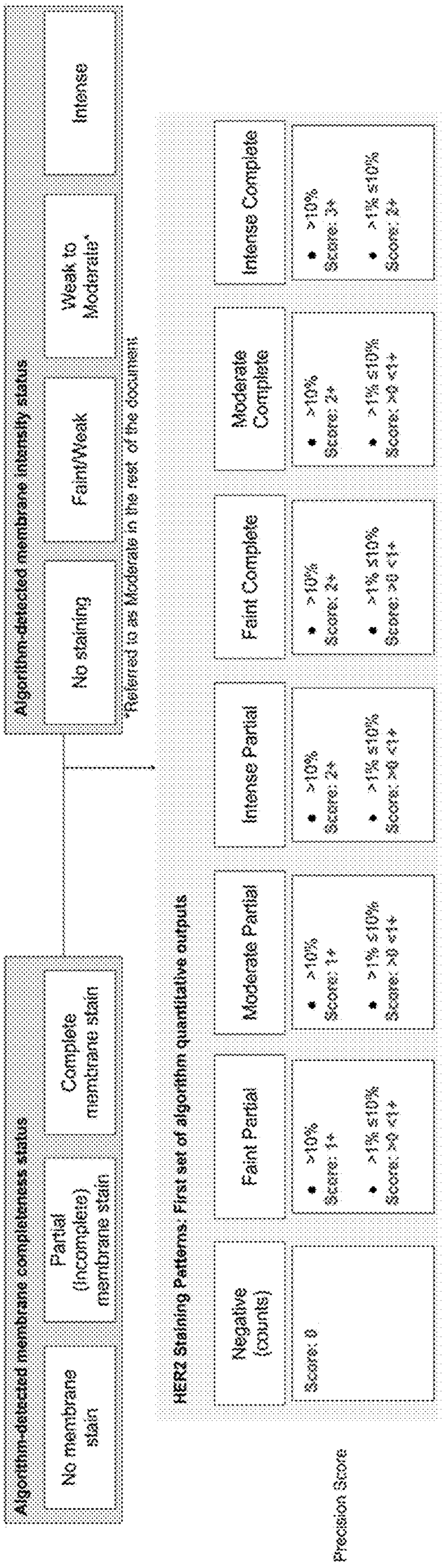

At blocks 130 and 140, one or more trained ML models (e.g., one or more of the first, second, third, and fourth CNNs described above) may be applied to generate HER2 cell-level features for each slide that reflect the number of HER2 stained cells on a slide. Additionally or alternately, one or more trained ML models may be applied to generate HER2 slide level scores that reflect the staining pattern and intensity of the tumor cells. For example, the slide level score may correspond to or result in a Precision score that is equivalent to the ASCO/CAP scoring guidelines, as shown in FIG. 2.

Figure 3:
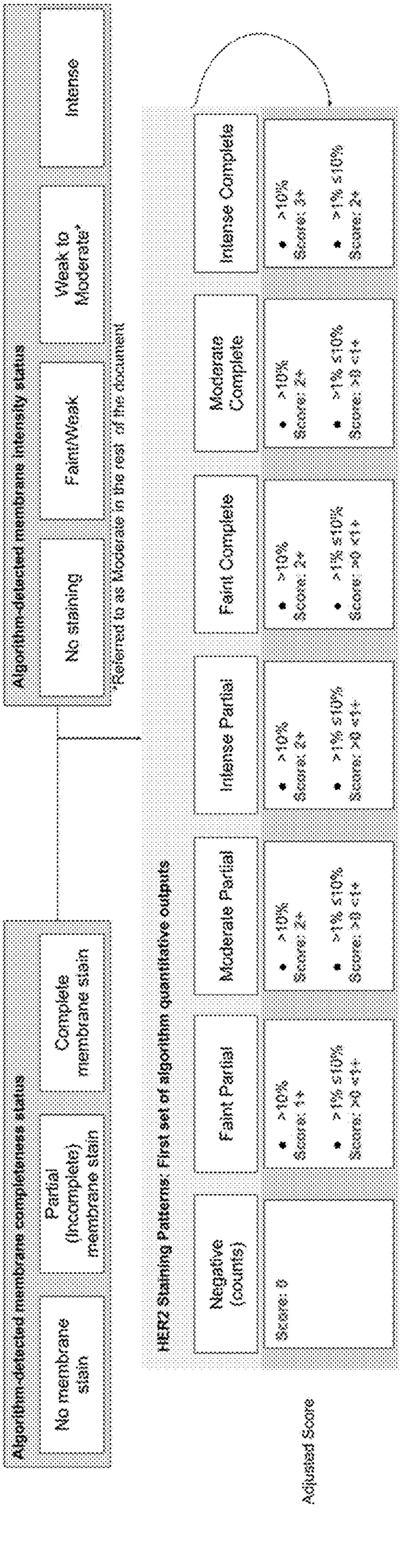
Figure 5:
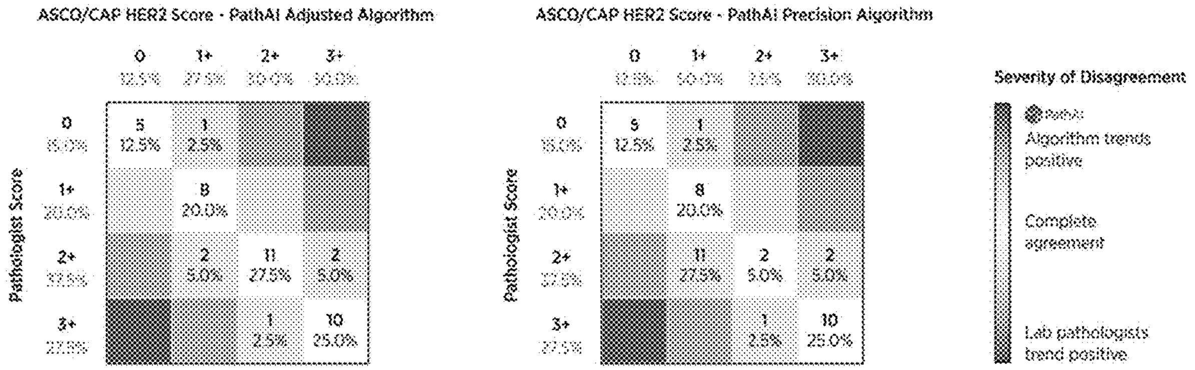

In some embodiments, to better agree with real-world scoring by pathologists, the ML models may be trained and optimized to generate Adjusted scores, as shown at block 150. The Adjusted scores may be in agreement with pathologist scores for each slide, as shown in FIG. 3. After analysis, a summary report may be generated that summarizes the outputs of the one or more ML models for each case (as shown in FIG. 4), for each trial overall (as shown in FIG. 5), or the like.

Experimental results obtained using the methods described herein have been reported. A total of 689 breast cancer tissue samples were obtained from various sources, including procured samples from Avaden Biosciences and anonymized samples from the AstraZeneca biobank. The breast cancer tissue samples included tissues from primary and metastatic tumors, core needle biopsies and surgical resections, lobular and ductal carcinomas, across tumor grades and HER2 expression levels reflecting real-world conditions. Samples were stained for HER2 detection (Ventana HER2 (4B5) Assay) and digitized (Leica Biosystems) across five laboratories in the US. Whole-slide images (WSIs) were stratified into training (n=407), validation (n=110), and test sets (n=172). Multiple convolutional neural network based ML models (PathAI, Boston, MA) were trained using 190,000 manual annotations provided by 30 board-certified pathologists to identify artifacts, invasive tumor, identify individual cancer cells and measure tumor cell membrane HER2 expression as partial or complete, and negative, weak-or-moderate, or intense. Cell-level scores were validated against a consensus of manual cell counts from 5 independent pathologists in 320 representative regions of test set WSIs. HER2 scores were generated by automatically applying rules derived from 2018 ASCO/CAP guidelines and then compared in the test set with consensus scores from 3 independent pathologists.

The cell counts provided by the ML model were consistent with cell counts obtained by pathologist consensus in all cell-types except for faintly positive HER2 cells, where ML-based quantification identified more cells on average. Accordingly, one advantageous result of the ML-model based scoring method disclosed herein was the identification of an ultra-low HER2 score, labeled >0<1+ (as shown in FIG. 6).

Automatically generated ML-ASCO/CAP HER2 scores using WSI showed consistency across IHC categories with the consensus of pathologists (ICC 0.88, 95% CI 0.82-0.92) in the test set and improved further when ML models were trained to agree with pathologists by adjusting cut offs (ICC 0.91, 95% CI 0.89-0.94). The ML-based model was deployed through the PathAI cloud platform to calculate HER2 testing quality control metrics in real-time in multicentric clinical trials.

Those skilled in the art would appreciate various advantages of the techniques disclosed in FIGS. 1-6. In some embodiments, these techniques may allow consistent, reproducible scoring of HER2 in each case at any clinical site where the QC tool is used. These techniques may generate two HER2 slide level scores (Precision and Adjusted). In some embodiments, the techniques may be more sensitive than pathologists and can detect an ultra-low level of HER2 (that corresponds to an ultra-low HER2 score that is not currently included in standard ASCO/CAP scoring guidelines but represents a patient population that may respond to HER2 therapeutics).

The embodiments described above are illustrative, and those skilled in the art would understand that numerous variations are possible. For example, the techniques may be applied on to other types of cancer where HER2 overexpression may be clinically significant including but not limited to gastric and esophageal cancer, ovarian, endometrial, bladder, lung, head and neck, and colon cancer. In some embodiments, the techniques may be applied to other types of anti-HER2 immunohistochemistry staining or alternative methods for visualizing HER2 protein on cellular membranes. In some embodiments, the techniques of FIGS. 1-6 may be modified to reflect any changes in ASCO/CAP HER2 scoring guidelines or adapted to alternative scoring guidelines that are incorporated into standard clinical practice.

The subject matter described herein can be implemented in digital electronic circuitry, or in computer software, firmware, or hardware, including the structural means disclosed in this specification and structural equivalents thereof, or in combinations of them. The subject matter described herein can be implemented as one or more computer program products, such as one or more computer programs tangibly embodied in an information carrier (e.g., in a machine readable storage device), or embodied in a propagated signal, for execution by, or to control the operation of, data processing apparatus (e.g., a programmable processor, a computer, or multiple computers). A computer program (also known as a program, software, software application, or code) can be written in any form of programming language, including compiled or interpreted languages, and it can be deployed in any form, including as a stand-alone program or as a module, component, subroutine, or other unit suitable for use in a computing environment. A computer program does not necessarily correspond to a file. A program can be stored in a portion of a file that holds other programs or data, in a single file dedicated to the program in question, or in multiple coordinated files (e.g., files that store one or more modules, sub programs, or portions of code). A computer program can be deployed to be executed on one computer or on multiple computers at one site or distributed across multiple sites and interconnected by a communication network.

The processes and logic flows described in this specification, including the method steps of the subject matter described herein, can be performed by one or more programmable processors executing one or more computer programs to perform functions of the subject matter described herein by operating on input data and generating output. The processes and logic flows can also be performed by, and apparatus of the subject matter described herein can be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processor of any kind of digital computer. Generally, a processor will receive instructions and data from a read only memory or a random access memory or both. The essential elements of a computer are a processor for executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. Information carriers suitable for embodying computer program instructions and data include all forms of nonvolatile memory, including by way of example semiconductor memory devices, (e.g., EPROM, EEPROM, and flash memory devices); magnetic disks, (e.g., internal hard disks or removable disks); magneto optical disks; and optical disks (e.g., CD and DVD disks). The processor and the memory can be supplemented by, or incorporated in, special purpose logic circuitry.

To provide for interaction with a user, the subject matter described herein can be implemented on a computer having a display device, e.g., a CRT (cathode ray tube) or LCD (liquid crystal display) monitor, for displaying information to the user and a keyboard and a pointing device, (e.g., a mouse or a trackball), by which the user can provide input to the computer. Other kinds of devices can be used to provide for interaction with a user as well. For example, feedback provided to the user can be any form of sensory feedback, (e.g., visual feedback, auditory feedback, or tactile feedback), and input from the user can be received in any form, including acoustic, speech, or tactile input.

The subject matter described herein can be implemented in a computing system that includes a back end component (e.g., a data server), a middleware component (e.g., an application server), or a front end component (e.g., a client computer having a graphical user interface or a web browser through which a user can interact with an implementation of the subject matter described herein), or any combination of such back end, middleware, and front end components. The components of the system can be interconnected by any form or medium of digital data communication, e.g., a communication network. Examples of communication networks include a local area network ("LAN") and a wide area network ("WAN"), e.g., the Internet.

It is to be understood that the disclosed subject matter is not limited in its application to the details of construction and to the arrangements of the components set forth in the following description or illustrated in the drawings. The disclosed subject matter is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods, and systems for carrying out the several purposes of the disclosed subject matter. It is important, therefore, that the claims be regarded as including such equivalent constructions insofar as they do not depart from the spirit and scope of the disclosed subject matter.

Although the disclosed subject matter has been described and illustrated in the foregoing exemplary embodiments, it is understood that the present disclosure has been made only by way of example, and that numerous changes in the details of implementation of the disclosed subject matter may be made without departing from the spirit and scope of the disclosed subject matter.

The invention claimed is:

1. A method for performing a diagnostic assessment based on digital pathology data, comprising:

obtaining first digital pathology data comprising intensity information, the first digital pathology data being associated with a plurality of regions of interest in a biological sample;

applying one or more first machine learning models to the first digital pathology data, the one or more first machine learning models identifying one or more first regions of interest among the plurality of regions of interest based on the intensity information;

applying one or more second machine learning models to the first digital pathology data, the one or more second machine learning models identifying at least one pattern associated with at least one of the one or more first regions of interest;

generating a diagnostic assessment based on the one or more first regions of interest and the at least one pattern; and detecting drift in diagnostic assessments performed by at least one pathologist in a clinical trial by comparing the generated diagnostic assessment with the pathologist diagnostic assessments, wherein detecting drift comprises detecting a change over time in at least one of nomenclature, grading of lesions, and scoring of a bio marker.

2. The method of claim 1, wherein the first digital pathology data comprises one or more whole slide images.

3. The method of claim 2, wherein the one or more whole slide images corresponds to a tumor biopsy sample stained using anti-HER2 immunohistochemistry.

4. The method of claim 3, wherein the diagnostic assessment comprises a HER2 score.

5. The method of claim 1, wherein the one or more first regions of interest comprises at least one of a tissue region of interest or a cell of interest.

6. The method of claim 5, wherein the at least one of the tissue region of interest or the cell of interest comprises one or more of a cancer epithelium, a cancer stroma, a ductal carcinoma in situ, a necrosis, a cell membrane, or an artifact.

7. The method of claim 1, wherein the least one pattern comprises a staining pattern of a cell membrane.

8. The method of claim 7, wherein the staining pattern is selected from a group consisting of: negative or unstained, partial positive, and complete positive.

9. The method of claim 1, wherein the diagnostic assessment comprises a precision slide-level score.

10. The method of claim 1, wherein the diagnostic assessment comprises an adjusted slide level score, the adjusted slide level score being generated using machine learning model predictions optimized for consensus between the adjusted slide level score and a slide level score provided by a pathologist.

11. The method of claim 1, further comprising applying one or more third machine learning models to the first digital pathology data, the one or more third machine learning models identifying an intensity associated with at least one of the one or more first regions of interest.

12. The method of claim 11, wherein the intensity corresponds to an intensity of staining of cell membranes, wherein the intensity is selected from a group consisting of: unstained, faintly stained, moderately stained, or completely stained.

13. The method of claim 1, further comprising extracting one or more histological features associated with the first digital pathology data.

14. The method of claim 1, further comprising calculating one or more cell-level features associated with the first digital pathology data.

15. The method of claim 14, wherein the one or more cell-level features are based on a number of cells corresponding to each American Society of Clinical Oncology/College of American Pathologists (ASCO/CAP) category identified in the first digital pathology data.

16. The method of claim 1, wherein the tumor biopsy sample is derived from a patient with breast cancer.

17. A system for performing a diagnostic assessment based on digital pathology data comprising:

at least one computer processor, wherein the at least one computer processor is configured to:

obtain first digital pathology data comprising intensity information, the first digital pathology data being associated with a plurality of regions of interest in a biological sample;

apply one or more first machine learning models to the first digital pathology data, the one or more first machine learning models identifying one or more first regions of interest among the plurality of regions of interest based on the intensity information;

apply one or more second machine learning models to the first digital pathology data, the one or more second machine learning models identifying at least one pattern associated with at least one of the one or more first regions of interest;

generate a diagnostic assessment based on the one or more first regions of interest and the at least one pattern; and detect drift in diagnostic assessments performed by at least one pathologist in a clinical trial by comparing the generated diagnostic assessment with the pathologist diagnostic assessments, wherein detecting drift comprises detecting a change over time in at least one of nomenclature, grading of lesions, and scoring of a bio marker.

18. The system of claim 17, wherein the first digital pathology data comprises one or more whole slide images, the one or more whole slide images corresponding to a tumor biopsy sample stained using anti-HER2 immunohistochemistry, and wherein the diagnostic assessment comprises a HER2 score.

19. The system of claim 17, wherein the one or more first regions of interest comprises at least one of a tissue region of interest or a cell of interest, the at least one of the tissue region of interest or the cell of interest comprising one or more of a cancer epithelium, a cancer stroma, a ductal carcinoma in situ, a necrosis, a cell membrane, or an artifact.

20. The system of claim 17, wherein the least one pattern comprises a staining pattern of a cell membrane, the staining pattern being selected from a group consisting of: negative or unstained, partial positive, and complete positive.

21. The system of claim 17, wherein the diagnostic assessment comprises:

a precision slide-level score; and an adjusted slide level score, the adjusted slide level score being generated using machine learning model predictions optimized for consensus between the adjusted slide level score and a slide level score provided by a pathologist.

22. The system of claim 17, further comprising:

applying one or more third machine learning models to the first digital pathology data, the one or more third machine learning models identifying an intensity associated with at least one of the one or more first regions of interest, wherein the intensity corresponds to an intensity of staining of cell membranes, wherein the intensity is selected from a group consisting of: unstained, faintly stained, moderately stained, or completely stained;

extracting one or more histological features associated with the first digital pathology data; and calculating one or more cell-level features associated with the first digital pathology data.

23. An article of manufacture for performing a diagnostic assessment based on digital pathology data comprising:

a non-transitory processor readable medium; and instructions stored on the medium;

wherein the instructions are configured to be readable from the medium by at least one computer processor and thereby cause the at least one computer processor to operate so as to:

obtain first digital pathology data comprising intensity information, the first digital pathology data being associated with a plurality of regions of interest in a biological sample;

apply one or more first machine learning models to the first digital pathology data, the one or more first machine learning models identifying one or more first regions of interest among the plurality of regions of interest based on the intensity information;

apply one or more second machine learning models to the first digital pathology data, the one or more second machine learning models identifying at least one pattern associated with at least one of the one or more first regions of interest;

generate a diagnostic assessment based on the one or more first regions of interest and the at least one pattern; and detect drift in diagnostic assessments performed by at least one pathologist in a clinical trial by comparing the generated diagnostic assessment with the pathologist diagnostic assessments, wherein detecting drift comprises detecting a change over time in at least one of nomenclature, grading of lesions, and scoring of a bio marker.

24. The article of manufacture of claim 23, wherein the first digital pathology data comprises one or more whole slide images, the one or more whole slide images corresponding to a tumor biopsy sample stained using anti-HER2 immunohistochemistry, and wherein the diagnostic assessment comprises a HER2 score.

25. The article of manufacture of claim 23, wherein the one or more first regions of interest comprises at least one of a tissue region of interest or a cell of interest, the at least one of the tissue region of interest or the cell of interest comprising one or more of a cancer epithelium, a cancer stroma, a ductal carcinoma in situ, a necrosis, a cell membrane, or an artifact.

26. The article of manufacture of claim 23, wherein the least one pattern comprises a staining pattern of a cell membrane, the staining pattern being selected from a group consisting of: negative or unstained, partial positive, and complete positive.

27. The article of manufacture of claim 23, wherein the diagnostic assessment comprises:

a precision slide-level score; and an adjusted slide level score, the adjusted slide level score being generated using machine learning model predictions optimized for consensus between the adjusted slide level score and a slide level score provided by a pathologist.

28. The article of manufacture of claim 23, further comprising:

applying one or more third machine learning models to the first digital pathology data, the one or more third machine learning models identifying an intensity associated with at least one of the one or more first regions of interest, wherein the intensity corresponds to an intensity of staining of cell membranes, wherein the intensity is selected from a group consisting of: unstained, faintly stained, moderately stained, or completely stained;

extracting one or more histological features associated with the first digital pathology data; and calculating one or more cell-level features associated with the first digital pathology data.

* * * * *